United States Patent
Vicenzi

(10) Patent No.: US 12,108,971 B2
(45) Date of Patent: Oct. 8, 2024

(54) BONE SCREW FOR THE TREATMENT OF BONE COLLAPSES OR DEFORMATIONS, IN THE CASE OF THE CHARCOT FOOT, AND INSERTION INSTRUMENT OF ANTI-MIGRATION ELEMENTS INTO THE BONE SCREW

(71) Applicant: Orthofix S.R.L., Bussolengo (IT)

(72) Inventor: Federico Vicenzi, Verona (IT)

(73) Assignee: ORTHOFIX S.R.L., Verona (IT)

( * ) Notice: Subject to any disclaimer, the term of this patent is extended or adjusted under 35 U.S.C. 154(b) by 827 days.

(21) Appl. No.: 16/609,904

(22) PCT Filed: May 3, 2018

(86) PCT No.: PCT/EP2018/061371
§ 371 (c)(1),
(2) Date: Oct. 31, 2019

(87) PCT Pub. No.: WO2018/202786
PCT Pub. Date: Nov. 8, 2018

(65) Prior Publication Data
US 2020/0155211 A1  May 21, 2020

(30) Foreign Application Priority Data

May 4, 2017 (IT) ........................ 102017000048446

(51) Int. Cl.
*A61B 17/86* (2006.01)
*A61B 17/17* (2006.01)
(Continued)

(52) U.S. Cl.
CPC ........ *A61B 17/863* (2013.01); *A61B 17/1725* (2013.01); *A61B 17/8615* (2013.01);
(Continued)

(58) Field of Classification Search
CPC ............ A61B 17/8605; A61B 17/8875; A61B 17/888; A61B 17/8685; A61B 17/8615;
(Continued)

(56) References Cited

U.S. PATENT DOCUMENTS 3,808,937 A * 5/1974 Roehrig ............. A61B 17/8615
411/407
4,858,601 A * 8/1989 Glisson .................. F16B 35/00
411/389
(Continued)

FOREIGN PATENT DOCUMENTS

EP        2047808 A2    4/2009
WO    WO 2011/072249 A1    6/2011

OTHER PUBLICATIONS

International Searching Authority / European Patent Office, "International Search Report," for PCT/EP2018/061371, mailed Nov. 16, 2018, 7 pages.

*Primary Examiner* — Marcela I. Shirsat
(74) *Attorney, Agent, or Firm* — Haynes and Boone, LLP

(57) ABSTRACT

A bone screw for Charcot foot includes a non-threaded intermediate portion between threaded tip and head portions. The intermediate portion is longer than the tip and head portions. The head portion has an outer diameter larger than the intermediate and tip portions. The screw includes at least one transverse hole on the intermediate portion with a circular cross-section which is arranged for inserting a pin to prevent migration of the screw. The screw includes a helical groove on the intermediate portion. The head portion is removably coupled to the intermediate portion by a shape coupling between two profiles which allows only one relative coupling orientation or at least two relative coupling orientations rotated by a specific angular distance with respect to each other. The head portion is coupled to the intermediate portion by a shape coupling between two profiles comprising a radial groove and a radial relief.

4 Claims, 19 Drawing Sheets

(51) Int. Cl.
*A61B 17/88* (2006.01)
*F16B 35/04* (2006.01)
*A61B 17/90* (2006.01)

(52) U.S. Cl.
CPC ........ *A61B 17/864* (2013.01); *A61B 17/8685* (2013.01); *A61B 17/8605* (2013.01); *A61B 2017/8655* (2013.01); *A61B 17/888* (2013.01); *A61B 17/90* (2021.08); *F16B 35/045* (2013.01)

(58) Field of Classification Search
CPC ................ A61B 17/863; A61B 17/864; A61B 2017/8655; F16B 35/00
See application file for complete search history.

(56) References Cited

U.S. PATENT DOCUMENTS

| | | | |
|---|---|---|---|
| 5,217,462 A * | 6/1993 | Asnis | A61B 17/888 606/301 |
| 6,663,656 B2 * | 12/2003 | Schmieding | B25B 23/1422 606/232 |
| 11,291,488 B1 * | 4/2022 | O'Flaherty | A61B 17/8875 |
| 2005/0152770 A1 * | 7/2005 | Tschakaloff | F16B 33/006 411/403 |
| 2005/0261695 A1 * | 11/2005 | Cragg | A61B 17/70 606/86 R |
| 2006/0264954 A1 * | 11/2006 | Sweeney, II | A61B 17/8685 606/328 |
| 2009/0248024 A1 | 10/2009 | Edwards et al. | |
| 2010/0114315 A1 * | 5/2010 | Manderson | A61B 17/863 606/301 |
| 2011/0060336 A1 | 3/2011 | Pool et al. | |
| 2012/0053639 A1 * | 3/2012 | Grant | A61B 17/864 606/301 |
| 2013/0046311 A1 | 2/2013 | Blake et al. | |
| 2013/0066382 A1 | 3/2013 | Martin | |
| 2016/0120661 A1 * | 5/2016 | Schell | A61B 17/8605 623/17.11 |
| 2017/0112552 A1 | 4/2017 | Sinnott et al. | |

* cited by examiner

BONE SCREW FOR THE TREATMENT OF BONE COLLAPSES OR DEFORMATIONS, IN THE CASE OF THE CHARCOT FOOT, AND INSERTION INSTRUMENT OF ANTI-MIGRATION ELEMENTS INTO THE BONE SCREW

CROSS REFERENCE TO RELATED APPLICATIONS

The present application is the U.S. national phase of International Application No. PCT/EP2018/061371, filed May 3, 2018, which designated the U.S. and claims priority to and the benefit of the Italian Application No. 102017000048446, filed May 4, 2017, both of which are hereby incorporated by reference in their entirety as if fully set forth below in its entirety and for all applicable purposes.

FIELD OF THE INVENTION

The present invention relates to an improved bone screw for the treatment of bone collapses and deformations, of the type comprising a threaded head having a larger diameter than a non-threaded stem and a threaded tip.

The invention also relates to an instrument for supporting the surgeon in inserting anti-migration elements into the screw implanted in the bone.

In particular, the invention finds a useful application in the treatment of structural collapses and bone deformations in the so-called Charcot foot, and the following description refers to use in the context of this application.

PRIOR ART

The Charcot neuro-osteoarthritis is a degenerative disease that may occur in patients suffering from neuropathy (in particular diabetic neuropathy) that causes a bone resorption at the level of the joints, sometimes associated with structural collapses and significant bone deformations. The most affected joint is the foot one and, in these cases, we talk about the Charcot foot.

In the case of the Charcot foot, often a collapse of the medial and lateral arch of the foot, with the consequent flattening of the foot itself, occurs.

In the technical field of the present invention it is known to use bone screws, generally cannulated, introduced into the bones to recreate and support the arches of the foot.

The actual bone screws employed in the treatment of the Charcot foot have a non-threaded stem with a large diameter, to support the patient's weight, a threaded tip and a head also threaded having an outer diameter larger than the stem and the tip.

The presence of an outer thread of the head and of the tip allows generating a compression of the bones crossed by the screw once implanted.

In FIG. 1 a radiographic image of the above described bone screws implanted in a patient's foot is reported.

Though advantageous under various aspects, and substantially responding to the current needs of the sector, the bone screws for the treatment of the Charcot foot known in the art have however some drawbacks, which are currently not solved.

A major drawback is linked to the high risk of infection encountered by patients suffering from the Charcot foot who have undergone the implantation of a bone screw.

Another fundamental drawback is instead linked to the long-term stability of the bone screw implanted in the patient's foot. In particular, the bone screw tends over time to move from the initial implant position, thus compromising the outcome of the treatment.

Document US 2013/066382 A1 discloses a bone screw for osteosynthesis having a partially threaded stem spaced between a tip and a head both of which being externally threaded; the head having an outer diameter larger than the stem and the tip. Said bone screw can include two throughholes specifically intended to receive a screw or a pin to block the rotations of the bone screw relative to bone fragments.

However, this document does not refer to the suitability for treating the Charcot foot and even to the problem of avoiding the migration of the bone screw.

The technical problem underlying the present invention is to conceive a bone screw for the treatment of bone collapses or deformations of the foot in the so-called Charcot foot, having improved structural and functional features and such as to ensure the stability of the screw implanted in the bone for the entire duration of the treatment.

The technical problem goes with that of conceiving an insertion instrument for the minimally invasive insertion of anti-migration elements into the implanted bone screw.

SUMMARY OF THE INVENTION

An improved bone screw for the treatment of bone collapses or deformations in the case of the so-called Charcot foot according to the present invention is defined in independent claim 1.

Advantageous embodiments of said improved bone screw are defined in corresponding dependent claims.

An insertion instrument according to present invention is described in the present disclosure.

The present invention also provides a kit for the treatment of the Charcot foot comprising a bone screw and an insertion instrument of the previously said type.

The kit for the treatment of the Charcot foot may also include at least one pin to be introduced into at least one hole of the bone screw.

The features and advantages of the bone screw and of the insertion instrument of the present invention will become clearer from the following description, of embodiments given as non-limiting examples with reference to the appended drawings.

DETAILED DESCRIPTION OF THE PREFERRED EMBODIMENTS

Figure 1:
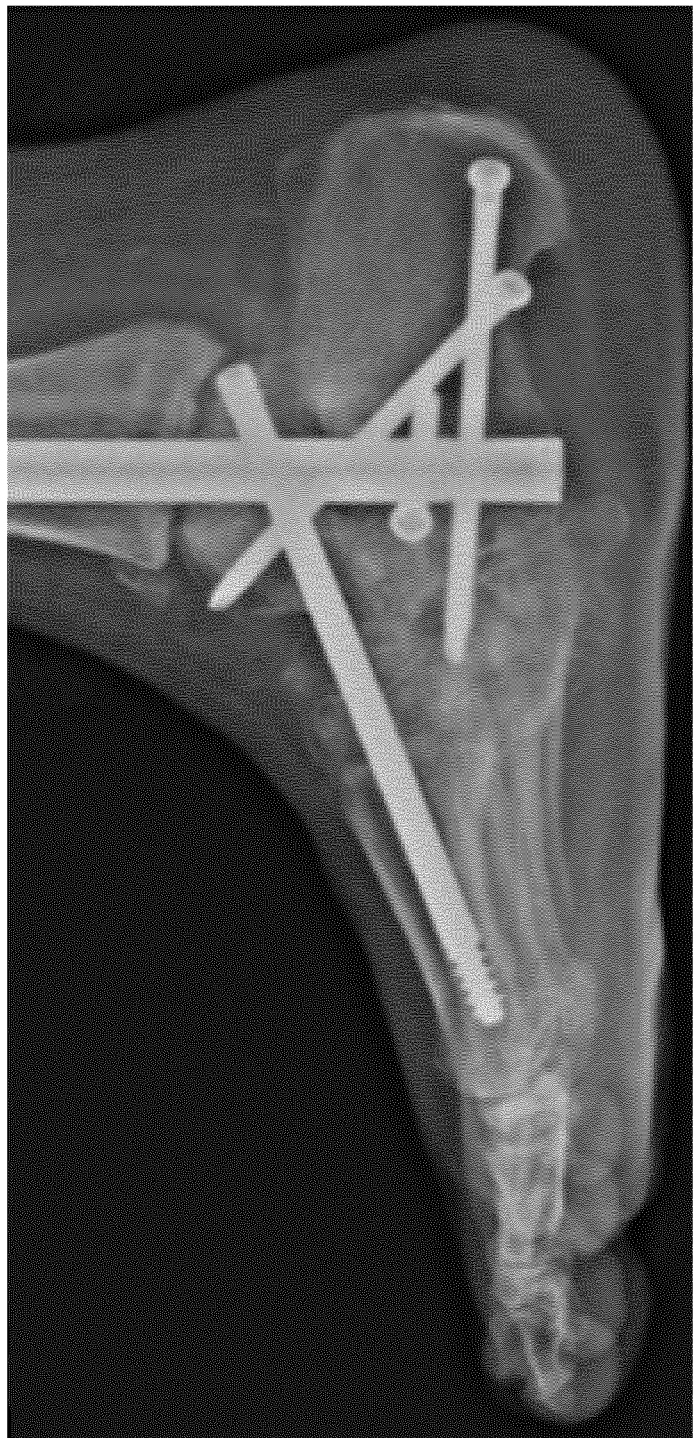
FIG. 1 shows a radiographic image of the bone screws according to the prior art implanted in a patient's foot.

With reference to said figures, and particularly to FIGS. 2-8, reference numbers 1 and 1' wholly and schematically indicate two different explanatory embodiments of a bone screw for the treatment of the Charcot foot, which has been improved to hinder the migration of the screw when implanted in the bone.

The following description is made with reference to the use of said application in the context.

Said bone screw 1, 1' has a substantially cylindrical shape and is preferably cannulated, so as to allow the guided insertion into the bone by means of a guidewire. As it can be noticed from the enclosed figures, the bone screw 1, 1' is made up of three consecutive portions, which are axially arranged: an intermediate portion 2 spaced between a tip portion 3 and a head portion 4.

The head portion 4 has an outer helical threading and an outer diameter greater than that of the other two portions 2, 3. The head portion 4 further comprises a hexagonal-hollowed head seat 5 for axially coupling with a tightening device. The head seat 5 has an inner profile wherein a radial recess 5a is formed (see FIG. 15) in order to ensure a unique coupling orientation of the tightening device, as it will become clearer in the rest of the description.

The tip portion 3 as well has an outer helical threading, in addition to a real bone screw tip 3a at the end having self-drilling features.

Unlike the other two portions 3, 4, the intermediate portion 2 has no threading, but it can have a helical groove 14 to facilitate osseointegration.

In a preferred embodiment, in the intermediate portion 2 at least one transverse through-hole 6 is formed, i.e. having hole axis orthogonal to the longitudinal axis of the bone screw 1, 1' and being accessible from two openings diametrically opposite to each other.

The hole 6 is conceived to house a pin 7 inserted and blocked in the hole 6 once the bone screw 1, 1' has been implanted in position in the patient's foot. The bone screw 1, 1' is implanted in position in the bone according to a known procedure, as in the case of the prior art bone screws shown in FIG. 1 implanted in a patient's foot.

Figure 9:
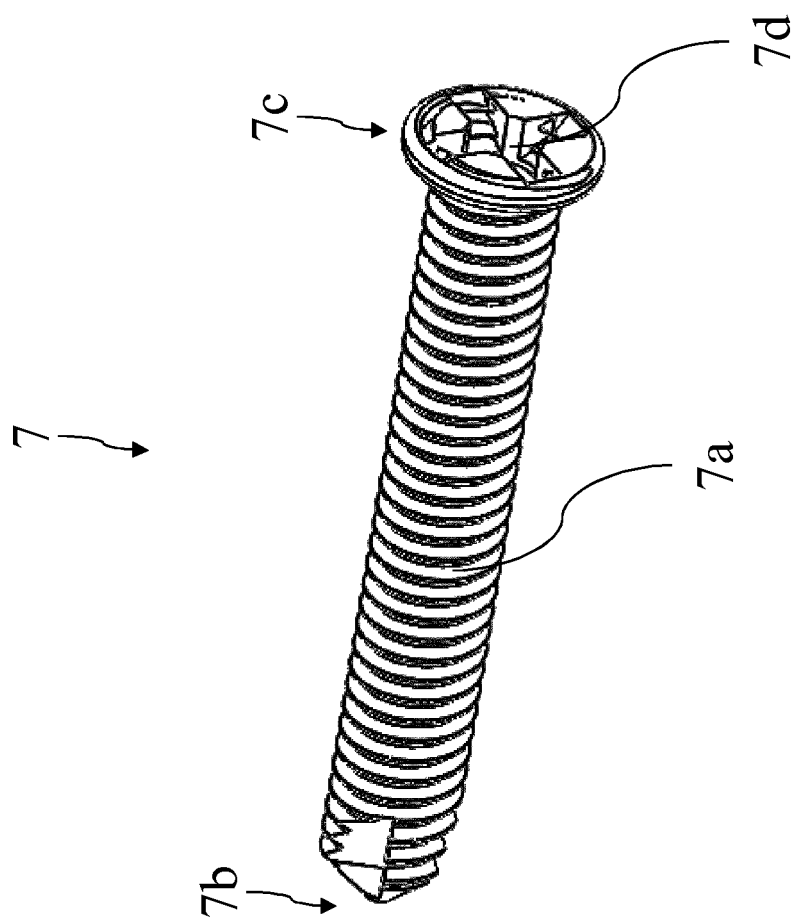
FIG. 9 shows a perspective view of an example of pin introducible into the bone screws of FIGS. 1 and 4.

FIG. 9 shows an example of pin 7 introducible into the hole 6 of the bone screw 1, 1'.

As it can be noticed from FIG. 9, the pin 7 is defined by a screw having reduced dimensions with respect to the bone screw 1, 1' that has an entirely threaded stem 7a, a self-drilling tip pin 7b and a pin head 7c with a seat of pin head 7d for coupling with a screwdriver.

Figure 2:
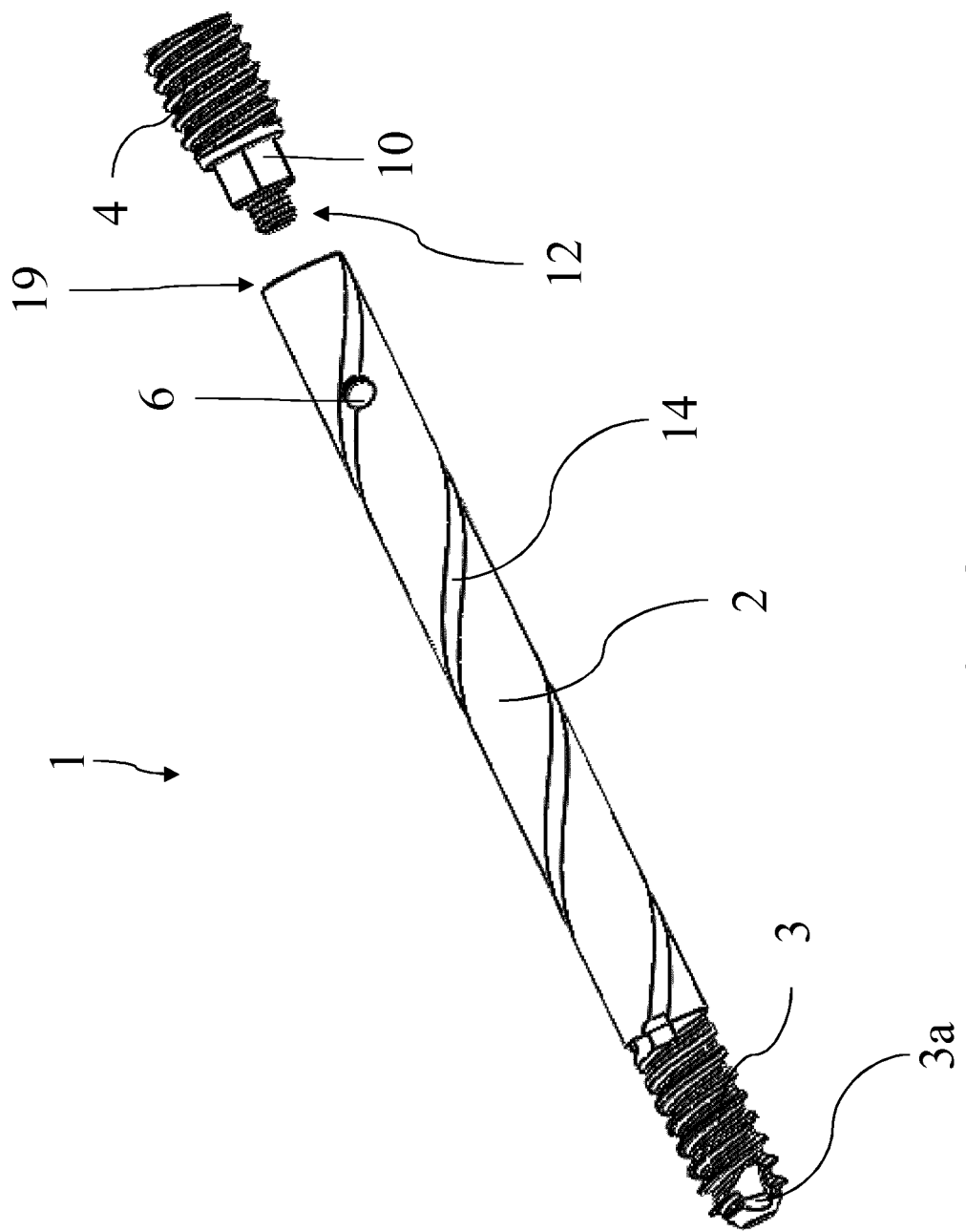
FIG. 2 shows a perspective view of a first embodiment of the bone screw according to the present invention, with decoupled head portion.
Figure 3:
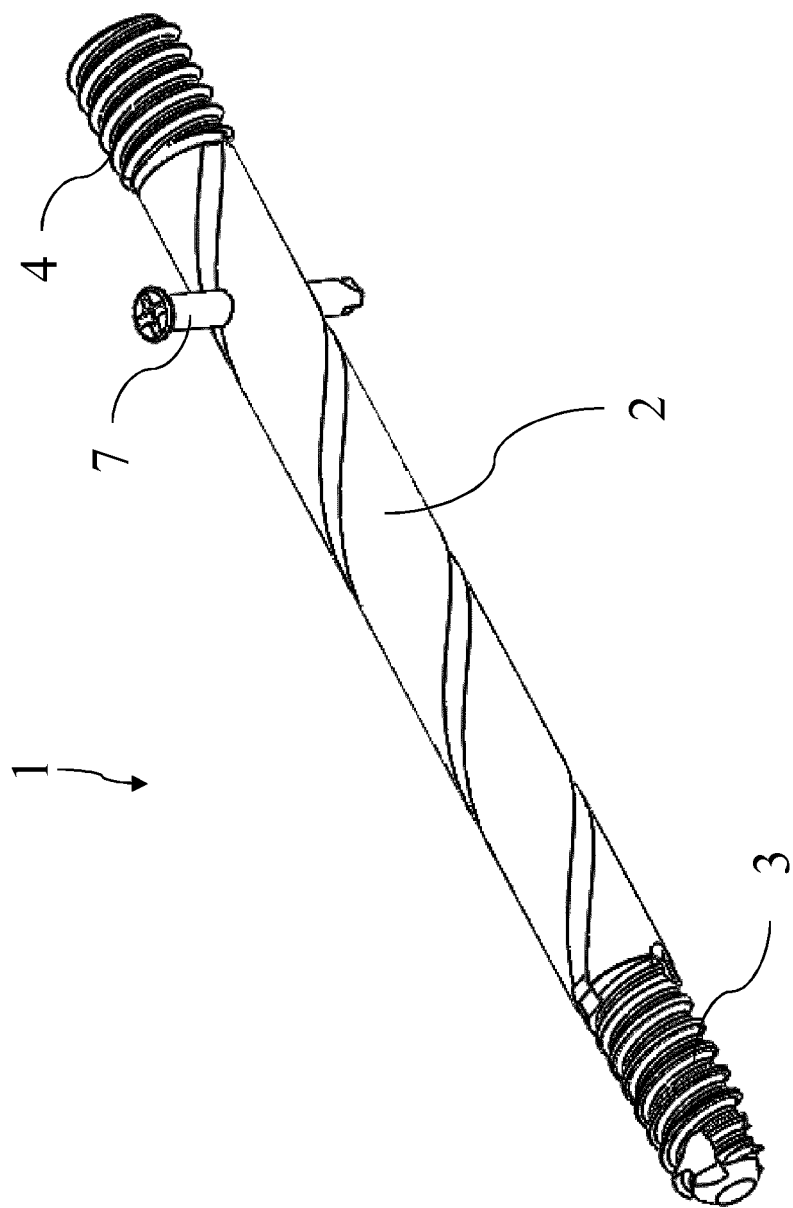
FIG. 3 shows a perspective view of the bone screw of FIG. 1 with head portion coupled and pin inserted.
Figure 4:
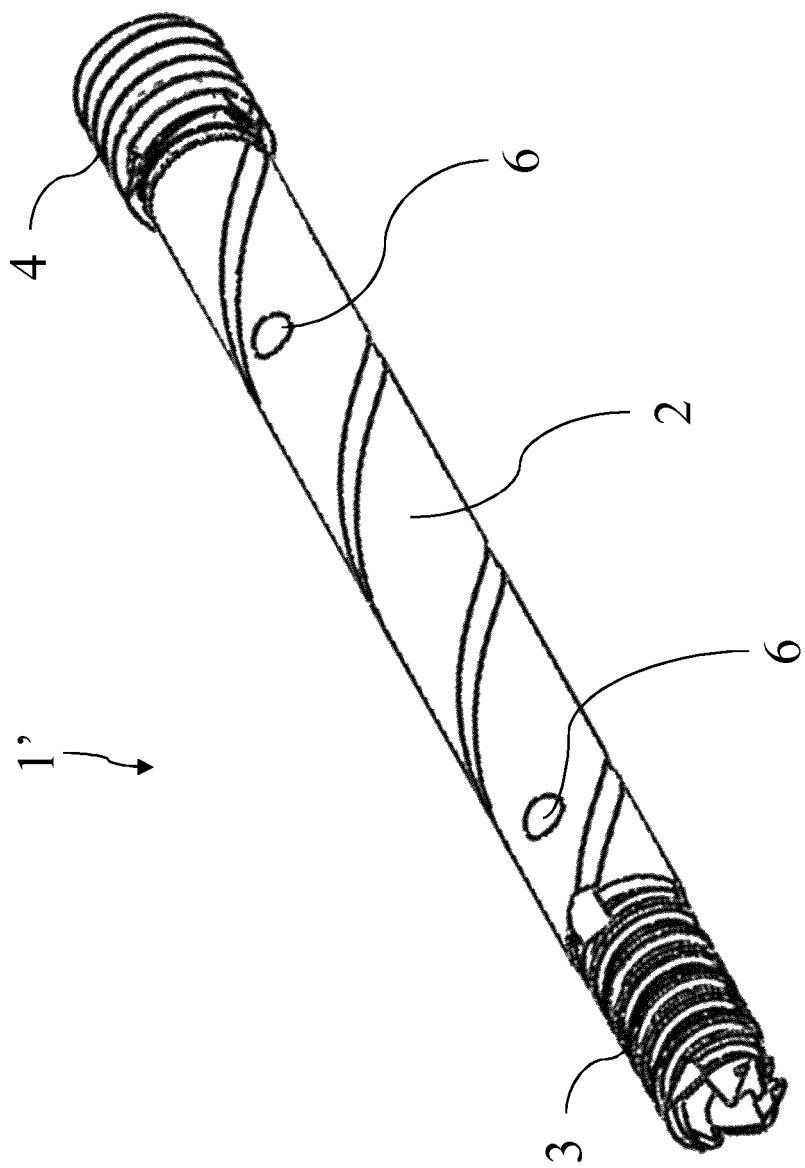
FIG. 4 shows a perspective view of a second embodiment of the bone screw made according to the present invention.
Figure 5:
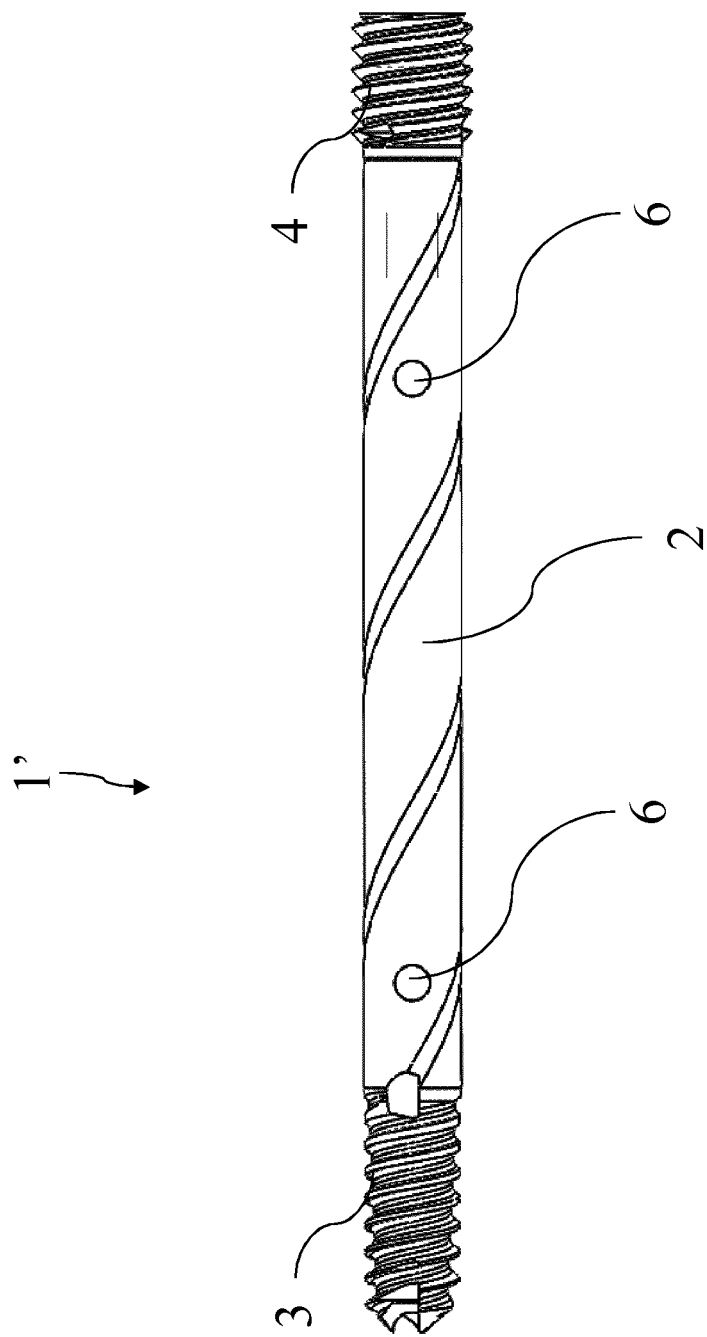
FIG. 5 shows a top view of the bone screw of FIG. 4.
Figure 6:
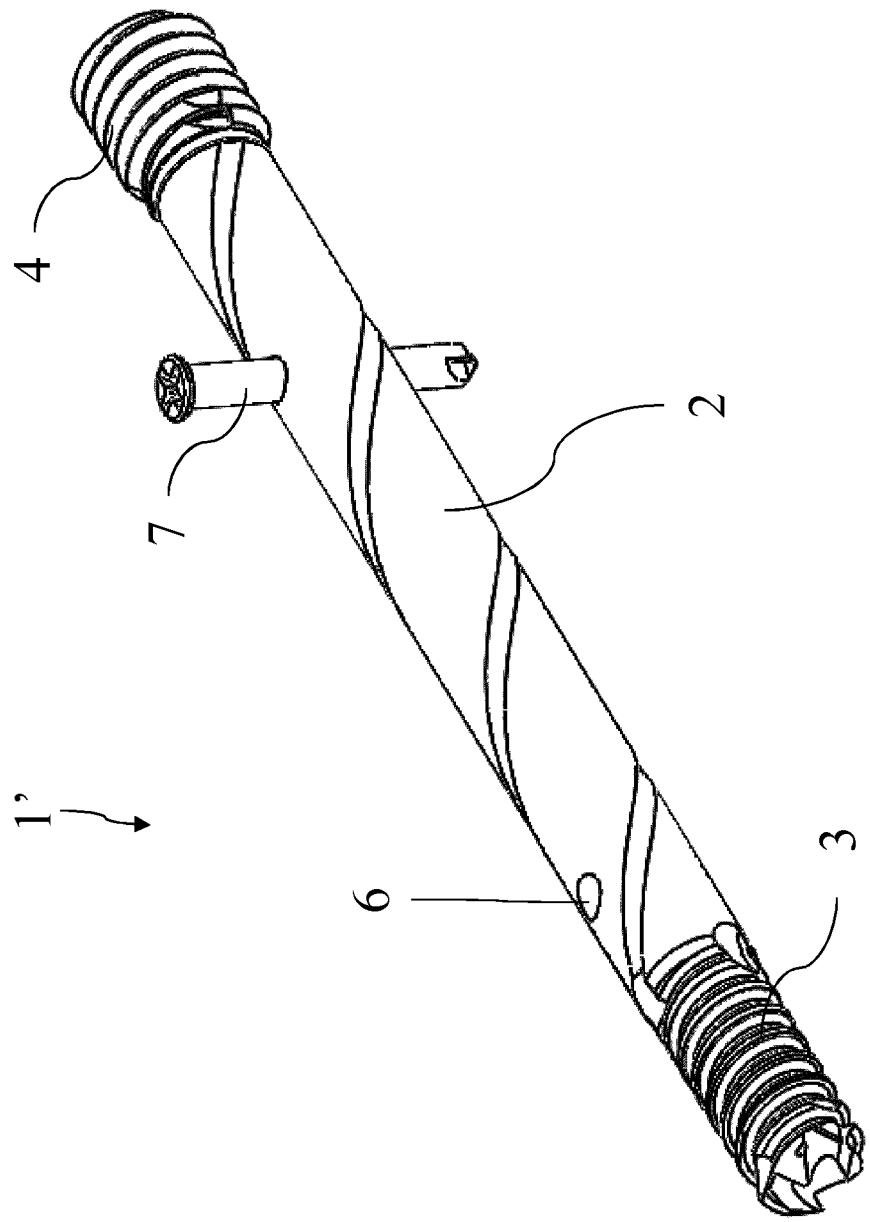
FIG. 6 shows a perspective view of the bone screw of FIG. 4 with a pin inserted.
Figure 7:
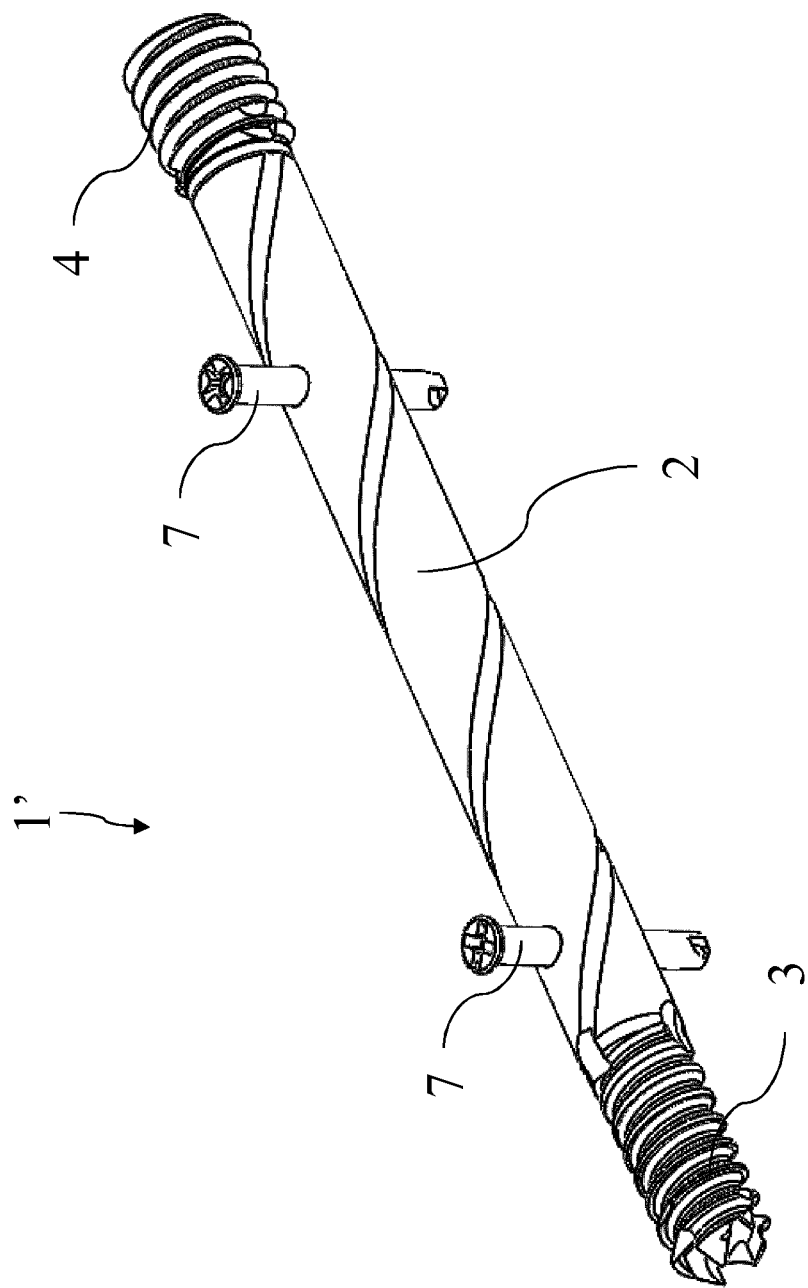
FIG. 7 shows a perspective view of the bone screw of FIG. 4 with both pins inserted.
Figure 8:
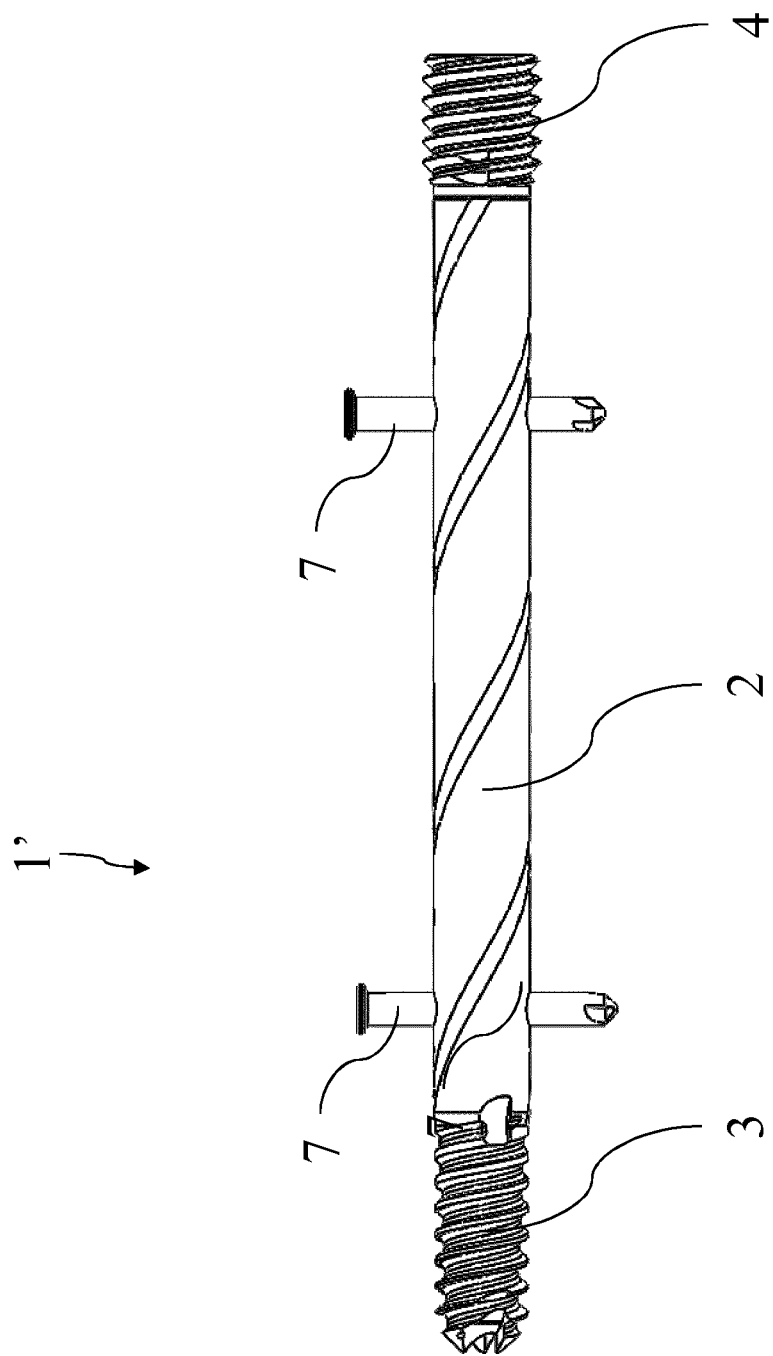
FIG. 8 shows a side view of the bone screw of FIG. 4 with both pins inserted.

FIGS. 2 and 3 show a first embodiment of the bone screw indicated with 1 having a single hole 6 formed close to the head portion 4.

FIGS. 4-8 instead show a second embodiment of the bone screw indicated with 1' having a further hole 6 formed close to the tip portion 3. The bone screw 1' differs from the bone screw 1 exclusively in the number of holes 6.

As it can be noticed in FIGS. 3, 6-8, the pin 7 inserted in the corresponding hole 6 transversally projects on opposite sides of the bone screw 1, 1', placing the projecting parts in contact with the bone surrounding the bone screw 1, 1' when implanted. This does not exclude alternative embodiments wherein the hole 6 is not a through-hole and the pin 7 can only project from one side of the bone screw 1, 1'. In other alternative embodiments, there may be more than one hole that is not a through-hole with different orientations rotated by a specific angular distance with respect to the each other; for example, three holes at 120° with respect to each other.

In both the described embodiments, the bone screw 1, 1' has a head portion 4 removably coupled to a coupling end 19 of the intermediate portion 2 away from the tip portion 3. In particular, FIG. 2 shows the bone screw 1 with decoupled head portion 4.

Alternative embodiments can obviously provide a head portion 4 made in one piece with the intermediate portion 2.

Figure 10:
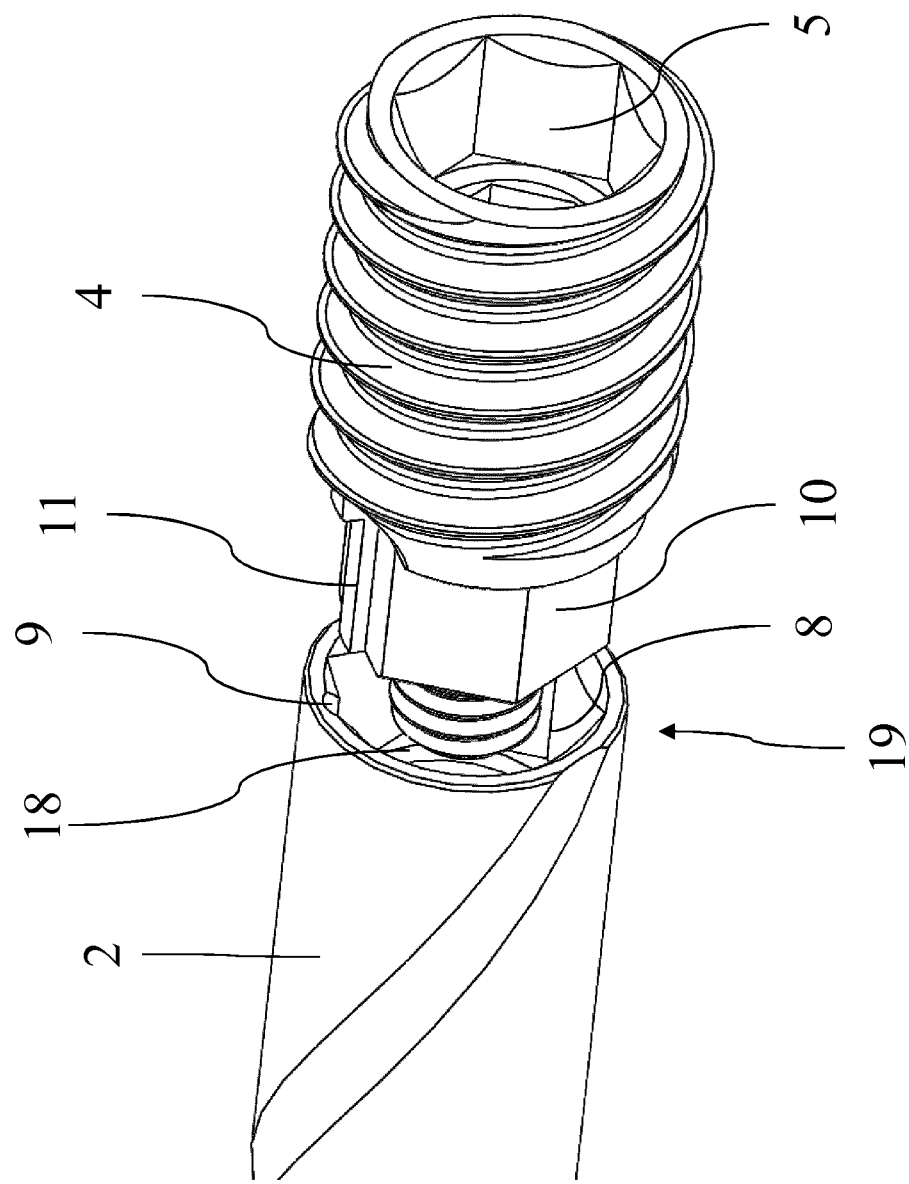
FIG. 10 shows a perspective view of a detail of the bone screw of FIGS. 1 and 4, with head portion decoupled.
Figure 11:
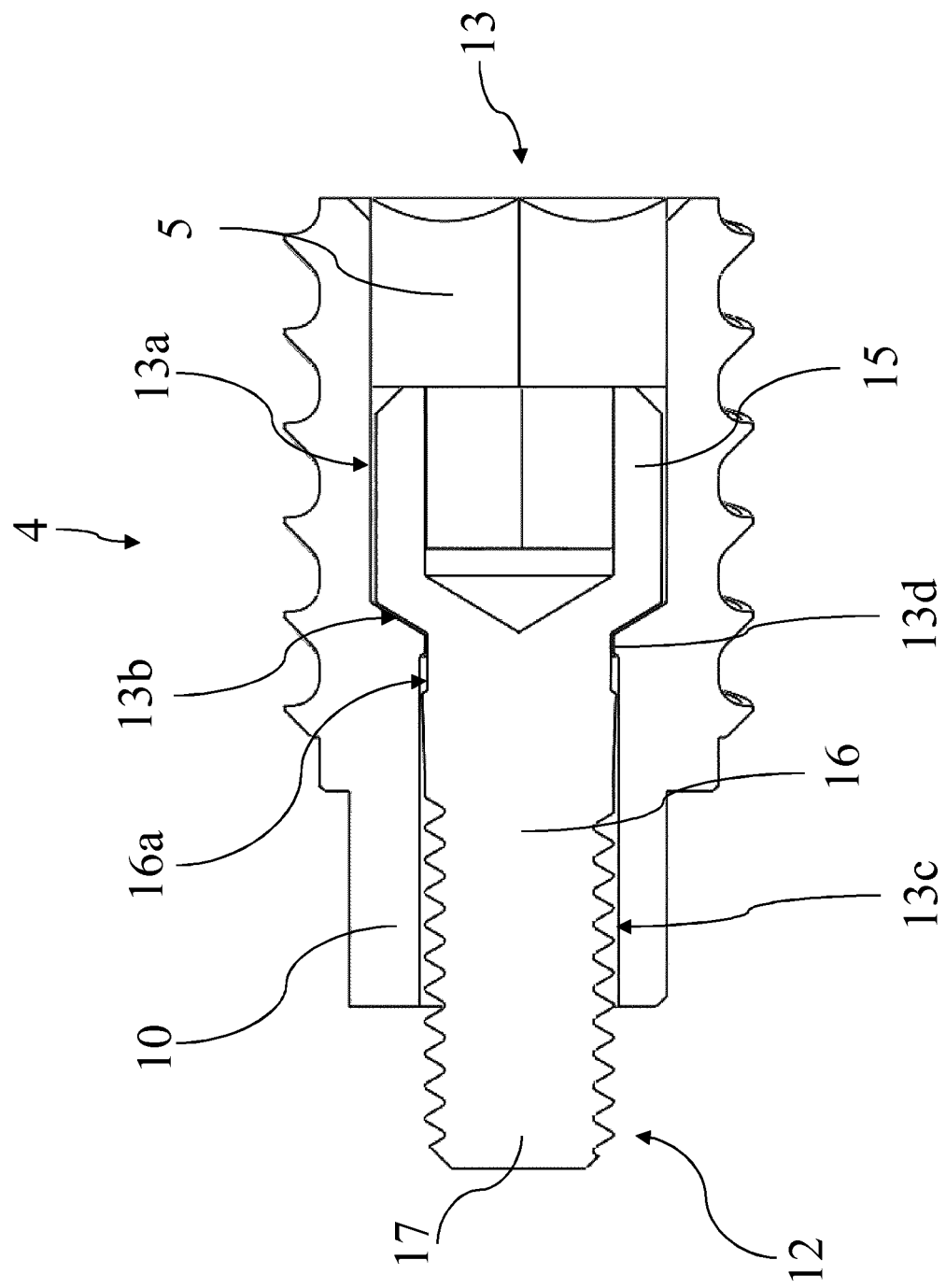
FIG. 11 shows a sectional view of the head portion of the bone screw of FIGS. 1 and 4.

With particular reference to FIGS. 10 and 11, the technical features of the coupling of the head portion 4 with the intermediate portion 2 will be hereinafter described.

As it can be noticed in FIG. 10, at the end opposite the head seat 5, the head portion 4 has a hexagonal-section male element 10 having a radial relief 11.

At the coupling end 19 of the intermediate portion 2 a hollow hexagonal-section female element 8 adapted to receive the male element 10 of the head portion 4 is formed. The female element 8 has a radial groove 9 to receive the relief 11 when the male element 10 is introduced in the female element 8.

The shape coupling just described, in addition to blocking the relative rotations, allows a unique relative coupling orientation between the intermediate portion 2 and the head portion 4. In fact, the coupling can only be carried out if the male element 10 is introduced into the female element 8, which is oriented so as to make the relief 11 slide within the groove 9. This does not exclude alternative embodiments wherein more than one relative coupling orientations rotated by a specific angular distance with respect to the each other are allowed.

In a preferred embodiment the advancement and fixing of the head portion 4 within the intermediate portion 2 are achieved by means of a tightening element 12.

The tightening element 12 is defined by a screw having a head 15 and a stem 16 that is partially threaded close to the tip 17. At the joint with the under-head, the stem 16 has a radial recess 16a that determines a localized reduction of the diameter of the stem 16 itself. Between the recess 16a and the threading the stem 16 is slightly tapered to facilitate the assembly with the head portion 4.

As it can be noticed in FIG. 11, the head portion 4 has an axial channel 13 extending along the entire length starting from the head seat 5. The axial channel 13 comprises a first section 13a communicating with the head seat 5 jointed through an inclined surface 13b to a second section 13c arranged to house the stem 16 of the tightening element 12. At the joint there is a radial tooth 13d that determines a localized narrowing of the diameter of the second section 13c.

Prior to proceeding with the coupling between the head portion 4 and the intermediate portion 2, the tightening element 12 is assembled to the head portion 4 since it is inserted through the head seat 5 in the axial channel 13 until the under-head of the head 15 abuts onto the inclined surface 13b and the tip 17 exits from the opposite end. The stem 16 is press-fitted until it goes past the tooth 13d that is housed within the recess 16a, axially blocking the tightening element 12 within the axial channel 13. The tightening element 12 is suitably dimensioned so as to be able to freely rotate about its own axis when inserted in the axial channel 13.

Once the tightening element 12 has been assembled to the head portion 4 as shown in FIG. 11, the advancement of the male element 10 within the female element 8, which are suitably oriented so as to align the relief 11 to the groove 9, is achieved by screwing the stem 16 within the inner threading 18 adjacent to the female element 8. FIG. 10 shows the head portion 4 suitably oriented prior to coupling with the intermediate portion 2.

The present invention further comprises an insertion instrument for the guided insertion of the pins 7 into the holes 6 of the bone screw 1, 1' once the bone screw 1, 1' has been implanted into the patient's foot.

In the rest of the description a preferred embodiment of the insertion instrument, indicated with reference number 20 and wholly represented in FIGS. 12, 13, 16 and 17, will be shown. By way of example the insertion instrument 20 applied to the bone screw 1' for inserting the pin 7 into the hole 6 close to the head portion 4 will be described.

The insertion instrument 20 comprises a centering device 50 axially coupled to a tightening device 30.

The tightening device 30 is defined by a substantially cylindrical bar 34 having a hexagonal-section tightening tip 35 at an end and a tightening handle 36 at the opposite end.

The tightening tip 35 has a hexagonal profile with a radial projection 37. The tightening tip 35 is dimensioned to be introduced into the head seat 5 of the bone screw 1' with a determined relative orientation such as to make the projection 37 slide within the recess 5a of the head seat 5 during the coupling.

In this way a shape coupling is achieved which, in addition to blocking the relative rotations, allows a unique relative coupling orientation between the head portion 4 of the bone screw 1' and the tightening tip 35 of the tightening device 30. This does not exclude alternative embodiments wherein more than one relative coupling orientations rotated by a specific angular distance with respect to the each other are allowed.

Figure 14:
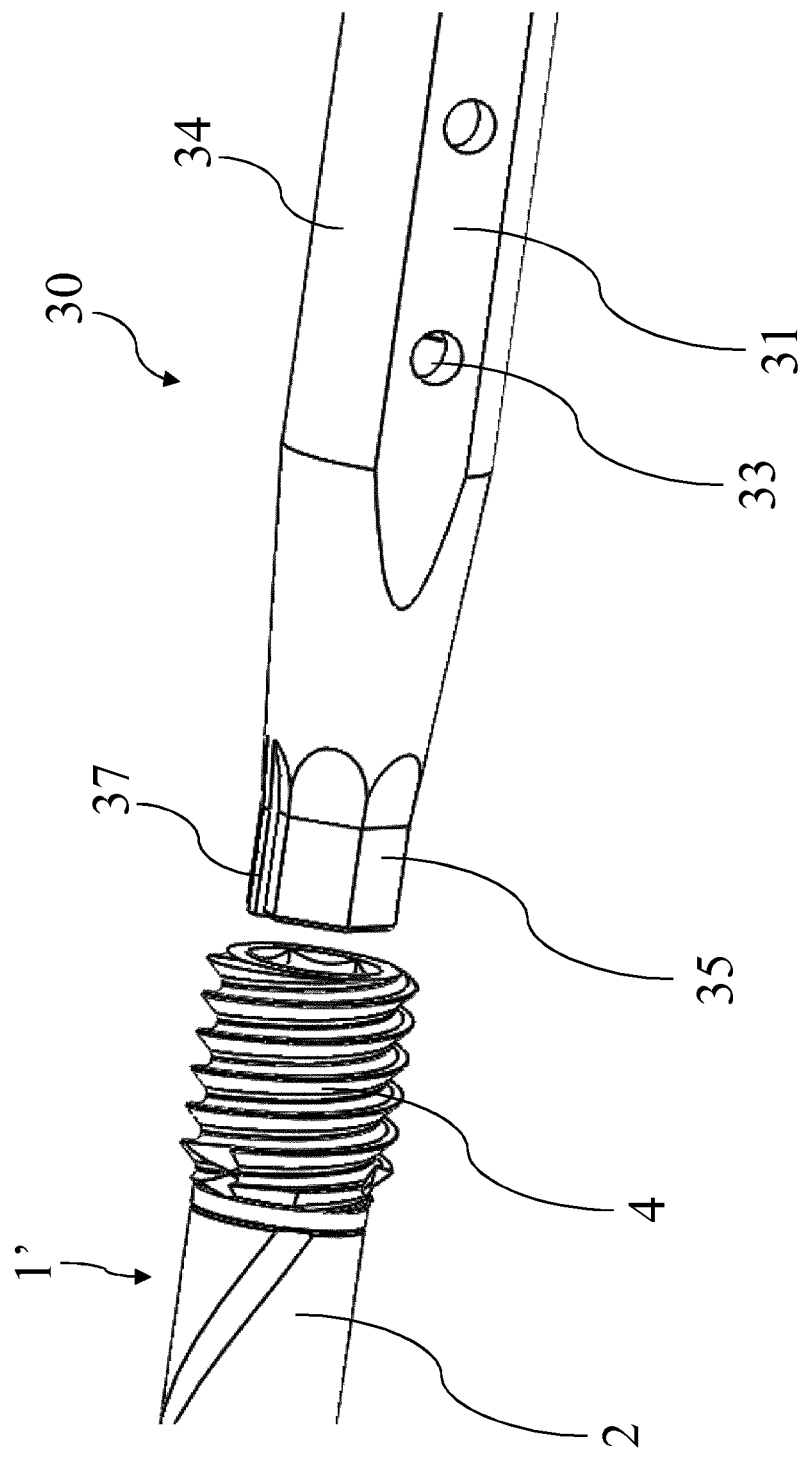
FIG. 14 shows a perspective view of a detail of the tightening device of the insertion instrument of FIG. 12 decoupled from the bone screw of FIG. 4.
Figure 15:
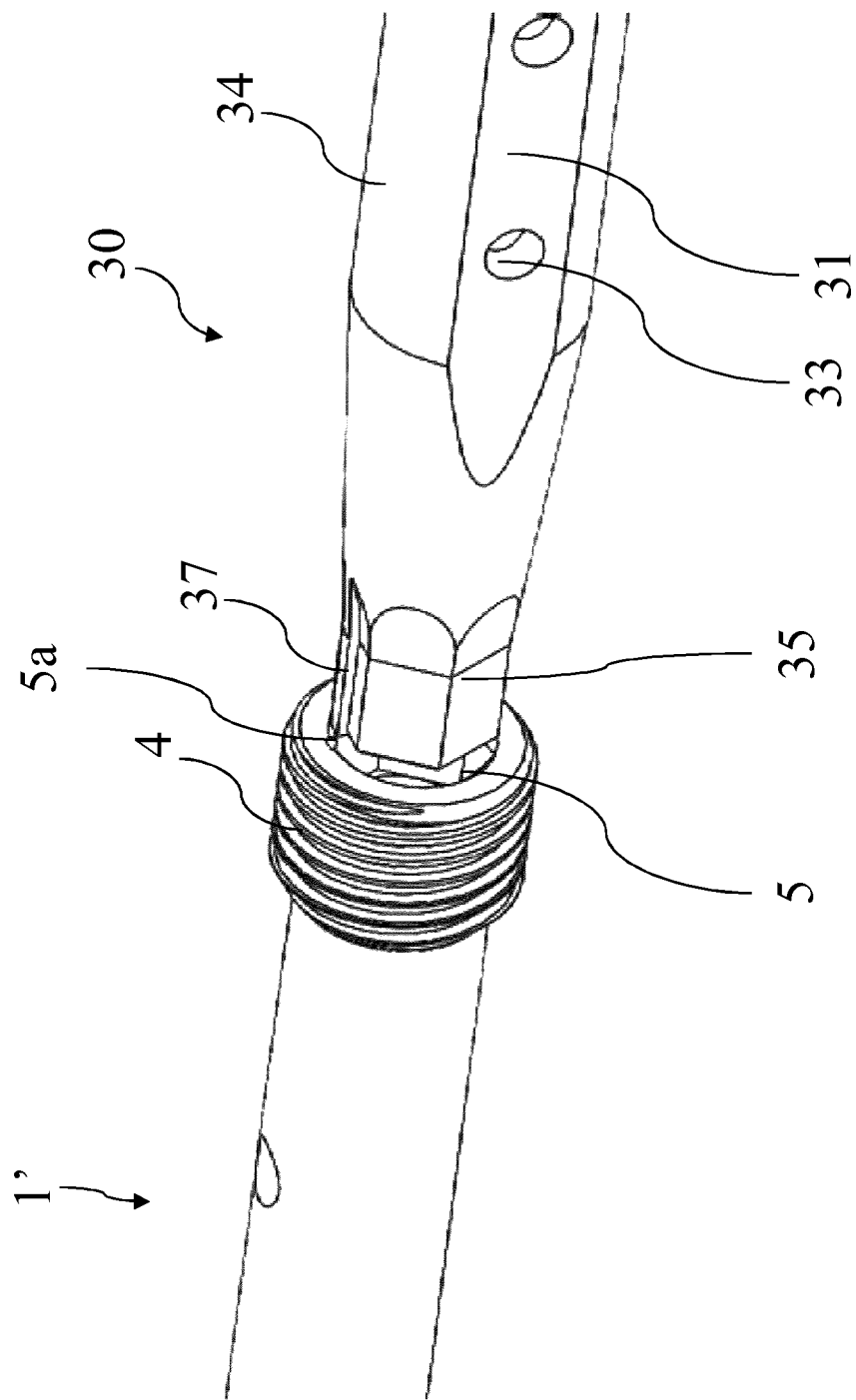
FIG. 15 shows a different perspective view of the detail of FIG. 14.

FIGS. 14 and 15 show the tightening tip 35 of the tightening device 30 suitably oriented prior to coupling with the head seat 5 of the head portion 4 of the bone screw 1'.

Along the bar 34 two elongated, parallel and diametrically opposite flattenings 31 are formed, which have centering seats 33. The centering seats 33 belong to the fastening means 32 used to removably fasten the centering device 50 to the tightening device 30, as it will become clearer in the rest of the description.

The centering device 50 is substantially L-shaped comprising a first part 54, elongated in the direction of a first part axis X, whereon an alignment through-opening 51 is formed having opening axis Y orthogonal to the first part axis X. The centering device 50 further comprises a second part 55 jointing the first part 54 to a third part 56 arranged to be coupled to the bar 34 of the tightening device 30.

The third part 56 is essentially U-shaped with a cavity 58 elongated in a direction parallel to the first part axis X and delimited by the second part 55 and by two parallel arms 57. Each arm 57 has an inner flat surface 52, facing the cavity 58 and lying on a plane parallel to the plane identified by the axes X and Y, and an outer surface 59 opposite and parallel to the corresponding flat surface 52. Each arm 57 also has orifices 60 that transversally pass through the arm 57 extending from the inner flat surface 52 to the outer surface 59.

Figure 16:
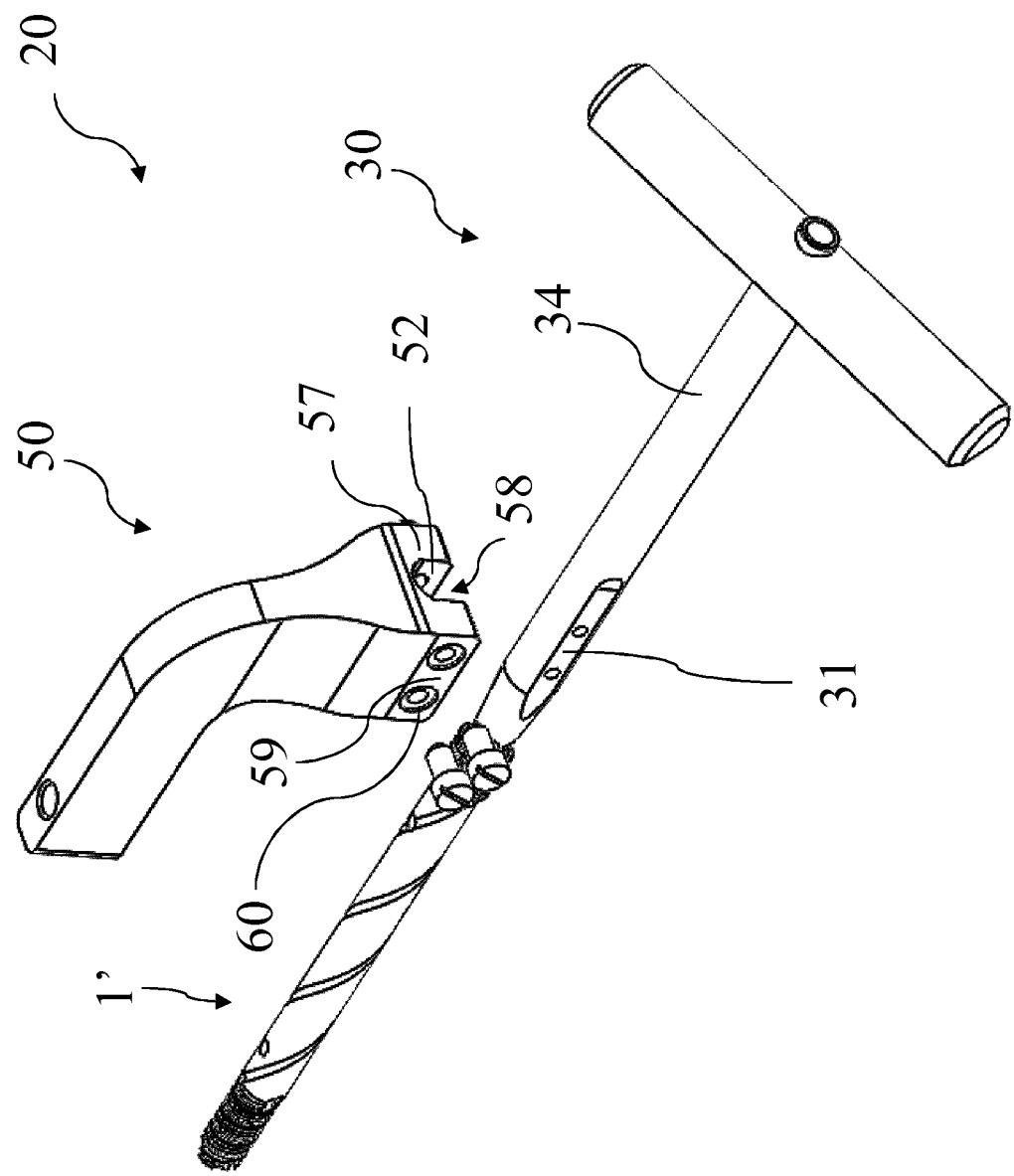
FIG. 16 shows a perspective view of the insertion instrument of FIG. 12 with tightening device coupled to the bone screw of FIG. 4 and centering device decoupled.
Figure 17:
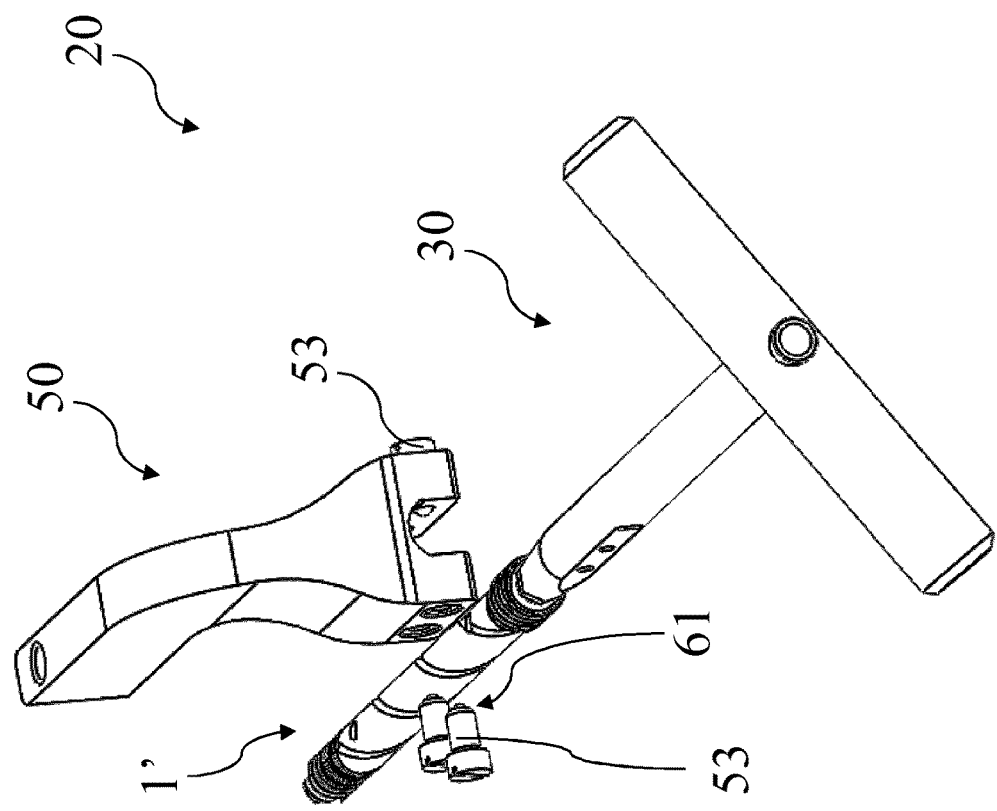
FIG. 17 shows a different perspective view of the insertion instrument of FIG. 12 with tightening device coupled to the bone screw of FIG. 4 and centering device decoupled.

In FIGS. 16 and 17 the centering device 50 decoupled from the tightening device 30 is shown.

The distance between the flat surfaces 52 is such as to allow the bar 34 of the tightening device 30 to be introduced into the cavity 58, placing each flat surface 52 in contact with the corresponding flattening 31 of the tightening device 30 so that, when the centering device 50 is coupled to the tightening device 30, the first part axis X is arranged parallel to the axis of the tightening device 30 and therefore to the axis of the bone screw 1'.

Moreover, the axial position of the flattenings 31 along the bar 34 of the tightening device 30 in relation to the length of the first part 54 and the angular orientation of the flattenings 31 with respect to the bar axis 34 are suitably defined so that the opening axis Y of the alignment opening 51 be perfectly coaxial to the axis of the hole 6 into which the pin 7 is intended to be introduced when the centering device 50 is coupled to the tightening device 30, which is in turn coupled to the head portion 5 of the bone screw 1'. Once the couplings have been properly defined, the above coaxiality is maintained even during the rotation of the tightening device 30 since the centering device 50 and the bone screw 1' are constrained to rotate in phase with the tightening device 30 itself.

Figure 12:
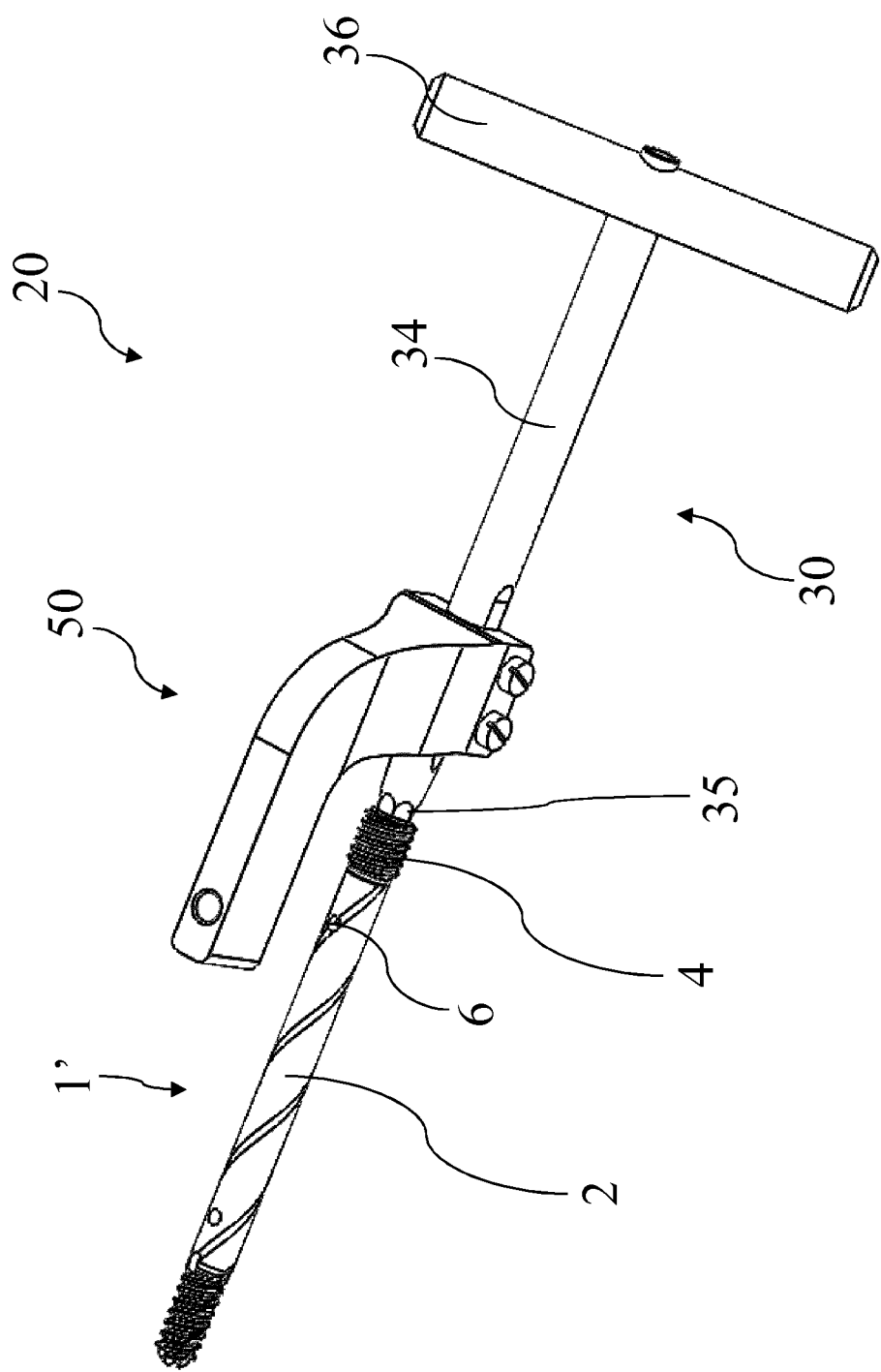
FIG. 12 shows a perspective view of the insertion instrument made according to the present invention with tightening device coupled to the bone screw of FIG. 4.
Figure 13:
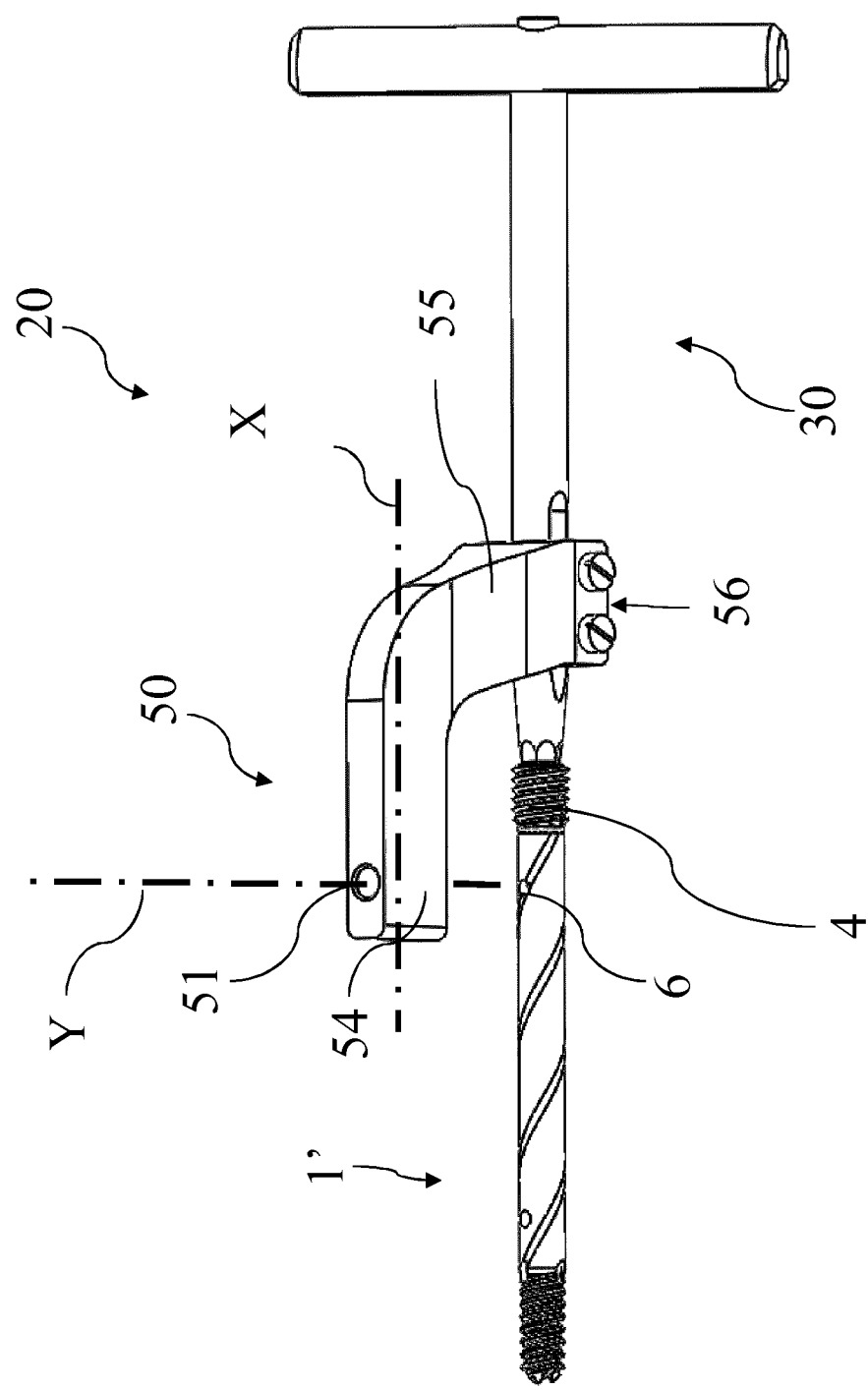
FIG. 13 shows a different perspective view of the insertion instrument of FIG. 12 with tightening device coupled to the bone screw of FIG. 4.

In FIGS. 12 and 13 the centering device 50 correctly coupled to the tightening device 30, which is in turn coupled to the bone screw 1', is shown.

The insertion instrument 20 further has snap fastening means 32 for removably blocking in position the centering device 50 when coupled to the tightening device 30.

The fastening means 32 comprise return elements 53 introduced through the outer surface 59 into the orifices 60 until they project from the flat surface 52. The return elements 53 are arranged to be snap fitted into the corresponding centering seat 33 of the tightening device 30 when the flat surfaces 52 of the centering device are placed in contact with the flattenings 31 of the tightening device 30 so as to align the return elements 53 to the corresponding centering seats 33.

Figure 18:
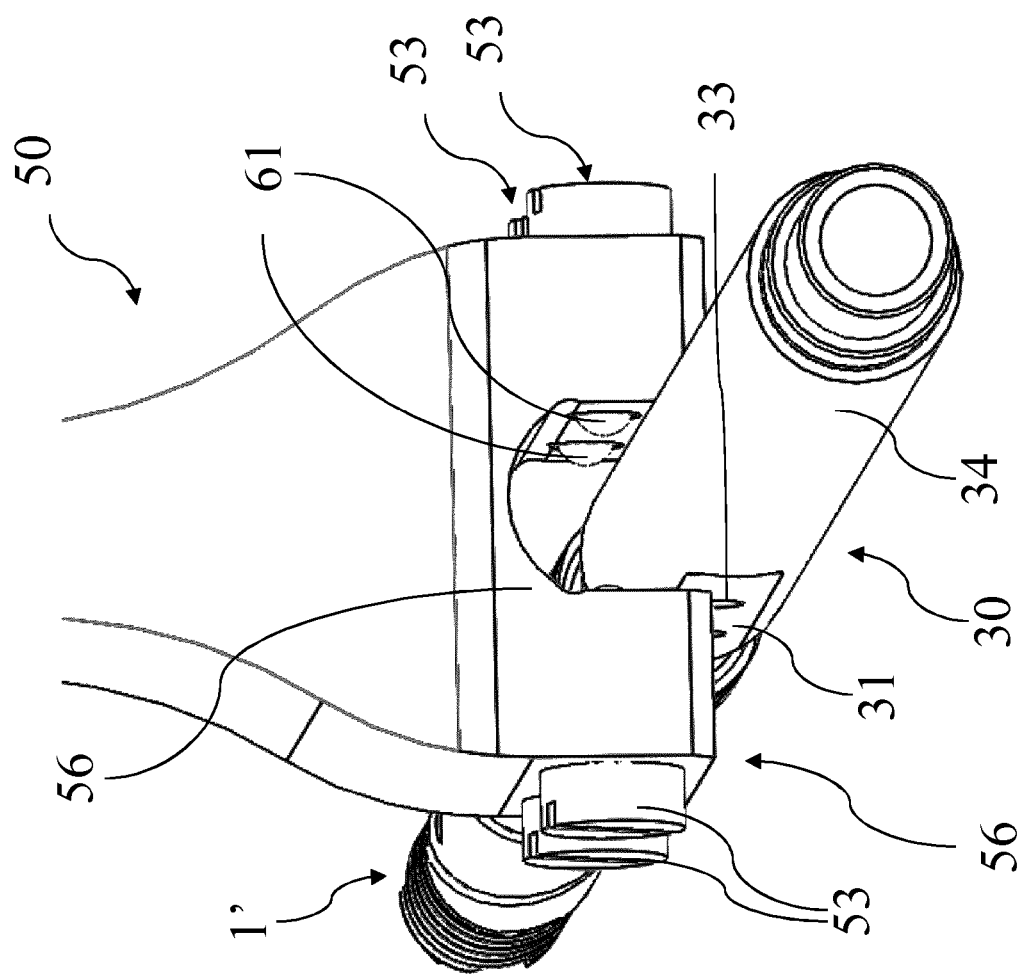
FIG. 18 shows a perspective view of a detail of the insertion instrument of FIG. 12 with centering device decoupled.
Figure 19:
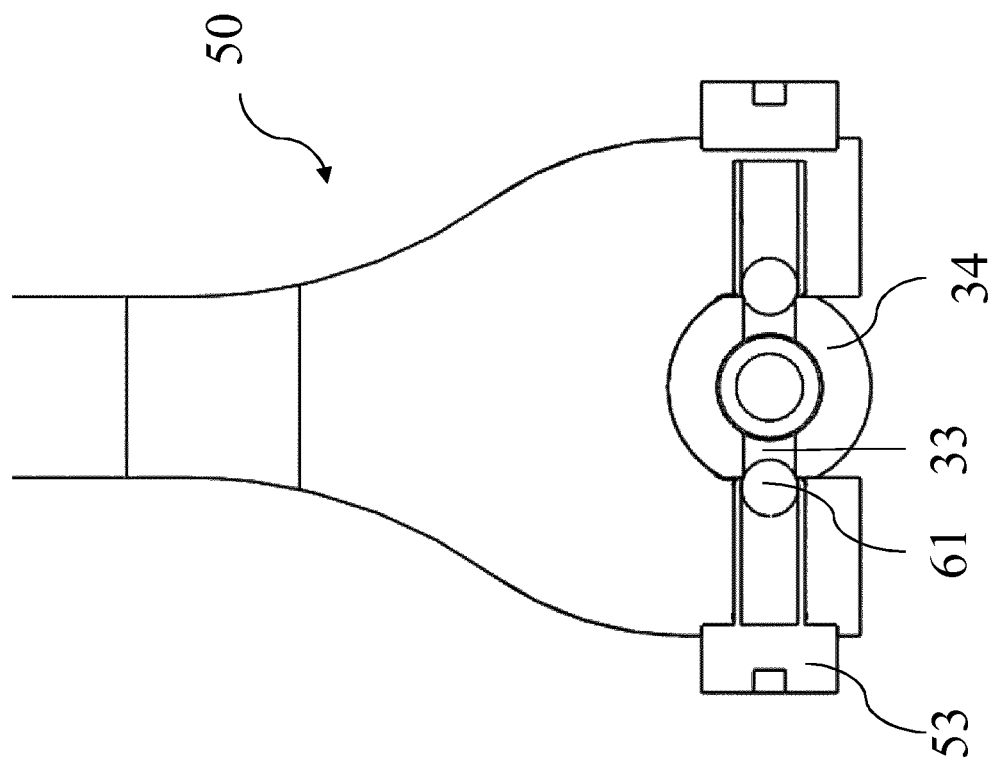
FIG. 19 shows a sectional view of a detail of the insertion instrument of FIG. 12 with centering device coupled.

In the preferred embodiment described, the return elements 53 consist of spring pressers provided at one end with a ball 61 which, when the return elements 53 are completely inserted in the orifice 60 and the centering device 50 is decoupled from the tightening device 30, project from the flat surfaces 52 within the cavity 58 (see FIG. 18). These balls 61 re-enter the return element 53 when placed in contact with the flattenings 31 and then return into the initial position when the return element 53 is aligned to the centering seat 33, penetrating the centering seat 33 itself. FIG. 19 shows a detail of the centering device 50 coupled to the tightening device 30, wherein the balls 61 are inserted within the centering seats 33.

The bone screw and the insertion instrument according to the invention solve the technical problem and achieve several advantages.

Advantageously, the described bone screw has at least one hole for inserting a pin, which, by transversally projecting, torsionally and axially constrains the screw to the surrounding bone, thus hindering the migration of the screw itself during the treatment.

Advantageously, the insertion instrument allows inserting the pins in a guided manner once the bone screw has already been implanted.

A further advantage consists in the fact that the insertion instrument allows a closed-sky insertion of the pins, i.e. the surgeon needs to make an incision having reduced dimensions, thus minimizing the risk of infection.

The invention claimed is:

1. An improved bone screw for the treatment of bone collapses and deformations in the case of the so-called Charcot foot, comprising a non-threaded intermediate portion spaced between a tip portion and a head portion both of which being externally threaded; wherein the non-threaded intermediate portion is longer than the tip portion; wherein the non-threaded intermediate portion is longer than the head portion; said head portion having an outer diameter larger than said intermediate portion and said tip portion; said head portion having a head seat for coupling a tightening device; said bone screw further comprising at least one transverse hole on the non-threaded intermediate portion, said transverse hole having a circular cross-section at both its inlet and outlet and being arranged for inserting a corresponding at least one pin to prevent the migration of said bone screw when implanted into the bone; said bone screw further comprising a helical groove on the non-threaded intermediate portion; wherein said head portion is removably coupled to said intermediate portion;

wherein said head portion is coupled to said intermediate portion by means of a shape coupling between two profiles, which allows only one relative coupling orientation or at least two relative coupling orientations rotated by a specific angular distance with respect to each other; wherein said head portion is coupled to said intermediate portion by means of a shape coupling between two profiles comprising a radial groove and a radial relief adapted to be inserted within said radial groove.

2. The bone screw according to claim 1, wherein said shape coupling between two profiles allows two relative coupling orientations rotated by 180° with respect to each other.

3. The bone screw according to claim 1, wherein one of said head portion and said intermediate portion has a female element with the radial groove; the other between said head portion and said intermediate portion having at least one male element with the radial relief adapted to be inserted within said radial groove when the shape coupling between said male element and said female element is achieved defining two relative coupling orientations rotated by 180° with respect to each other.

4. The bone screw according to claim 1, wherein one of said head portion and said intermediate portion has a female element defining a polygonal seat, at least a face of said polygonal seat comprising a radial groove; the other between said head portion and said intermediate portion having at least one male element defining a polygonal profile adapted to engage in said polygonal seat, at least a face of said polygonal profile having an elongated radial ridge adapted to slide within the radial groove.

* * * * *